US00PP18239P2

(12) United States Plant Patent
Tellwright

(10) Patent No.: US PP18,239 P2
(45) Date of Patent: Nov. 20, 2007

(54) ***NEMESIA* PLANT NAMED 'FLEURCEL'**

(50) Latin Name: *Nemesia×hybrida*
Varietal Denomination: FLUERCEL

(76) Inventor: Martine Tellwright, Highground House, Highground Lane, Barnham, West Sussex (GB), PO22 OBU ( * ) Notice: Subject to any disclaimer, the term of this patent is extended or adjusted under 35 U.S.C. 154(b) by 15 days.

(21) Appl. No.: 11/437,482

(22) Filed: May 19, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

UPOV ROM GTITM Computer Database, GTI Jouve Retrieval Software 2006/04 Citation for Fleurcel.*

* cited by examiner

*Primary Examiner*—Wendy C. Haas

(57) ABSTRACT

A new and distinct cultivar of *Nemesia* plant named 'FLEURCEL' that is characterized by compact upright habit, large cerise-red flowers, and green foliage. In combination these characteristics set 'FLEURCEL' apart from all other existing varieties of *Nemesia* known to the inventor.

2 Drawing Sheets

Genus: *Nemesia*.
Species: ×*hybrida*.
Denomination: 'FLEURCEL'.

BACKGROUND OF THE INVENTION

The present invention relates to a new and distinct cultivar of *Nemesia* plant grown as an ornamental for use in borders, hanging basket or flower bed. The new variety is known botanically as *Nemesia×hybrida* and will be referred to hereinafter by the cultivar name 'FLEURCEL'.

The new *Nemesia* cultivar named 'FLEURCEL' resulted from a formal breeding program that was conducted by the inventor at the inventor's nursery in West Sussex, United Kingdom. The purpose of the breeding program was to produce new varieties of *Nemesia* that exhibited improved flower size, new flower color, and compact habit. Three other varieties that have resulted from this breeding program are:

'FLEURIPI' (U.S. Plant Pat. No. 16,851).

'FLEURFLAME' (U.S. Plant Pat. No. 17,035).

'FLEURBAC' (U.S. Plant Pat. No. 16,931).

The new *Nemesia* variety named 'FLEURCEL' is a selection arising from controlled cross-pollination that began in 1998 and proceeded as follows.

(All of the seedling plants referenced herein by number are unreleased, unpatented selections retained by the inventor from previous generations).

*Nemesia* seedling 111 was crossed with *Nemesia* seedling 110 to produce *Nemesia* seedling 152.

*Nemesia* seedling 110 was crossed with *Nemesia* seedling 145 to produce *Nemesia* seedling 168.

*Nemesia* seedling 152 was then crossed with *Nemesia* seedling 168 and produced 'FLEURCEL'. The seed parent is *Nemesia* seedling 152 (unpatented) and the pollen parent is *Nemesia* seedling 168 (unpatented). Cross-pollination of the parents took place in West Sussex, United Kingdom in 2002. 'FLEURCEL' is one of the seedlings that was selected from this cross. The distinguishing characteristics that make 'FLEURCEL' unique from all other *Nemesia* known to the inventor are compact upright habit, large flower size, and cerise-red flowers.

'FLEURCEL' is distinguishable from the female parent by flower color and disease resistance. Seedling 152 exhibits large dark-blue flowers, and is prone to disease, whereas 'FLEURCEL' exhibits cerise-red flowers and is not susceptible to the diseases that affects seedling 152. 'FLEURCEL' is distinguishable from the male parent by plant habit, and flower color. Seedling 168 exhibits compact habit, and mauve flowers, each with a large yellow eye, compared to 'FLEURCEL', which exhibits compact upright habit and cerise-red flowers each with a small yellow eye.

The two closest comparison plants known to the inventor are *Nemesia* 'FLEURAME' (U.S. patent application Ser. No. 11/095,139, filed Mar. 30, 2005), and *Nemesia* 'FLEURBAC' (U.S. patent application Ser. No. 11/138,003, filed May 27, 2005).

'FLEURCEL' is distinguishable from 'FLEURAME' by plant height and flower color. 'FLEURCEL' is distinguishable from 'FLEURBAC' by plant height and flower color. 'FLEURBAC' exhibits bi-colored flowers, and both 'FLEURAME' and 'FLEURAME' are short in height compared to 'FLEURCEL'.

'FLEURCEL' was first asexually propagated in 2002 at the inventor's nursery in West Sussex, United Kingdom. The asexual propagation was conducted by the inventor and the method utilized was softwood cuttings. The inventor has determined that 'FLEURCEL' is stable and uniform, and reproduces true to type in successive generations of asexual reproduction.

SUMMARY OF THE INVENTION

The following traits have been repeatedly observed and represent the distinguishing characteristics of 'FLEURCEL'. In combination these traits set the new cultivar apart from all other existing varieties of *Nemesia* known to the inventor.

'FLEURCEL' has not been tested under all possible conditions and phenotypic differences may be observed with variations in environmental, climatic, and cultural conditions, without however, any variance in genotype.

1. 'FLEURCEL' exhibits compact upright habit.
2. 'FLEURCEL' exhibits large cerise-red flowers.
3. 'FLEURCEL' exhibits green foliage.
4. Growing conditions of 'FLEURCEL' include peat and bark soil, fertilizer, normal daylight, and adequate but not excess water.
5. 'FLEURCEL' is asexually propagated utilizing the method of softwood cuttings.
6. 'FLEURCEL' is hardy to minus 6° Centigrade.
7. 'FLEURCEL' is grown for use as a border plant, hanging basket, or bedding plant.

BRIEF DESCRIPTION OF THE DRAWINGS

The accompanying color drawings illustrate the overall appearance of the new *Nemesia* cultivar named 'FLEURCEL' showing the colors as true as it is reasonably possible to obtain in colored reproductions of this type. Colors in the drawings may differ from the color values cited in the detailed botanical description, which accurately describe the actual colors of the new variety 'FLEURCEL'. Plants are 8-months-old, in 1-liter containers and were grown under greenhouse conditions in Encinitas, Calif.

The drawing labeled

The drawing labeled

BOTANICAL DESCRIPTION OF THE PLANT

Figure 1:
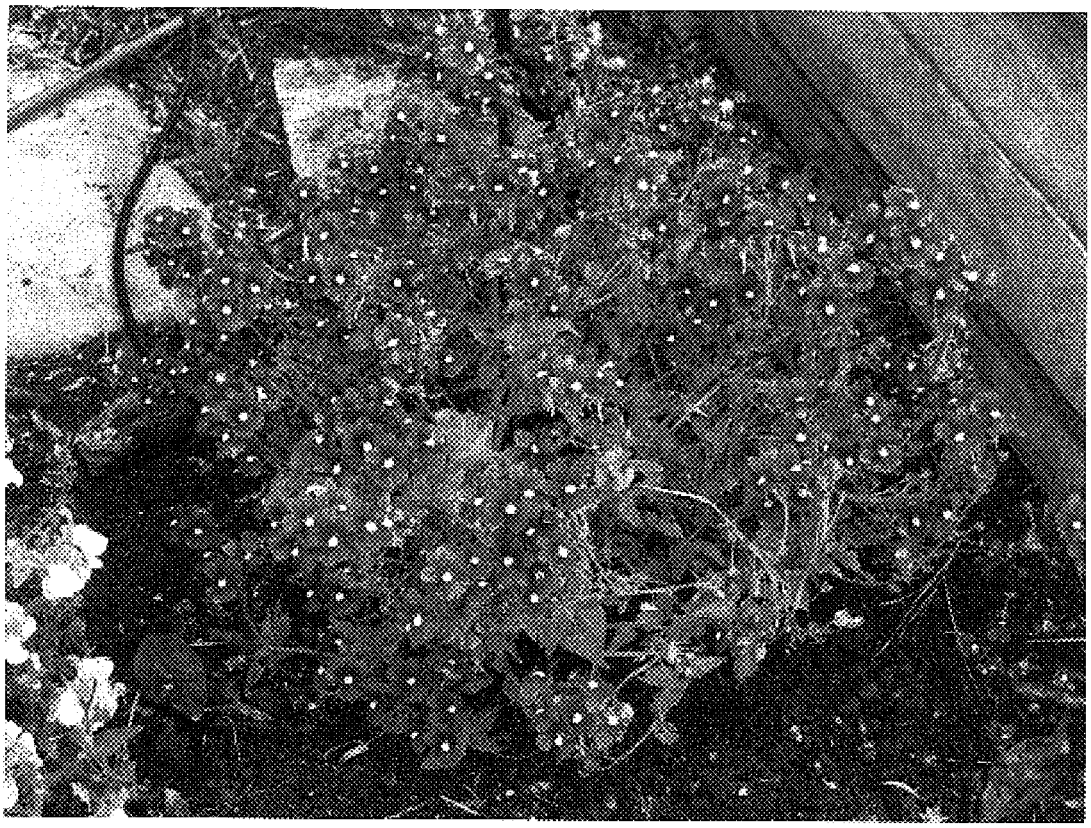
FIG. 1 depicts a side view illustrating plant habit.
Figure 2:
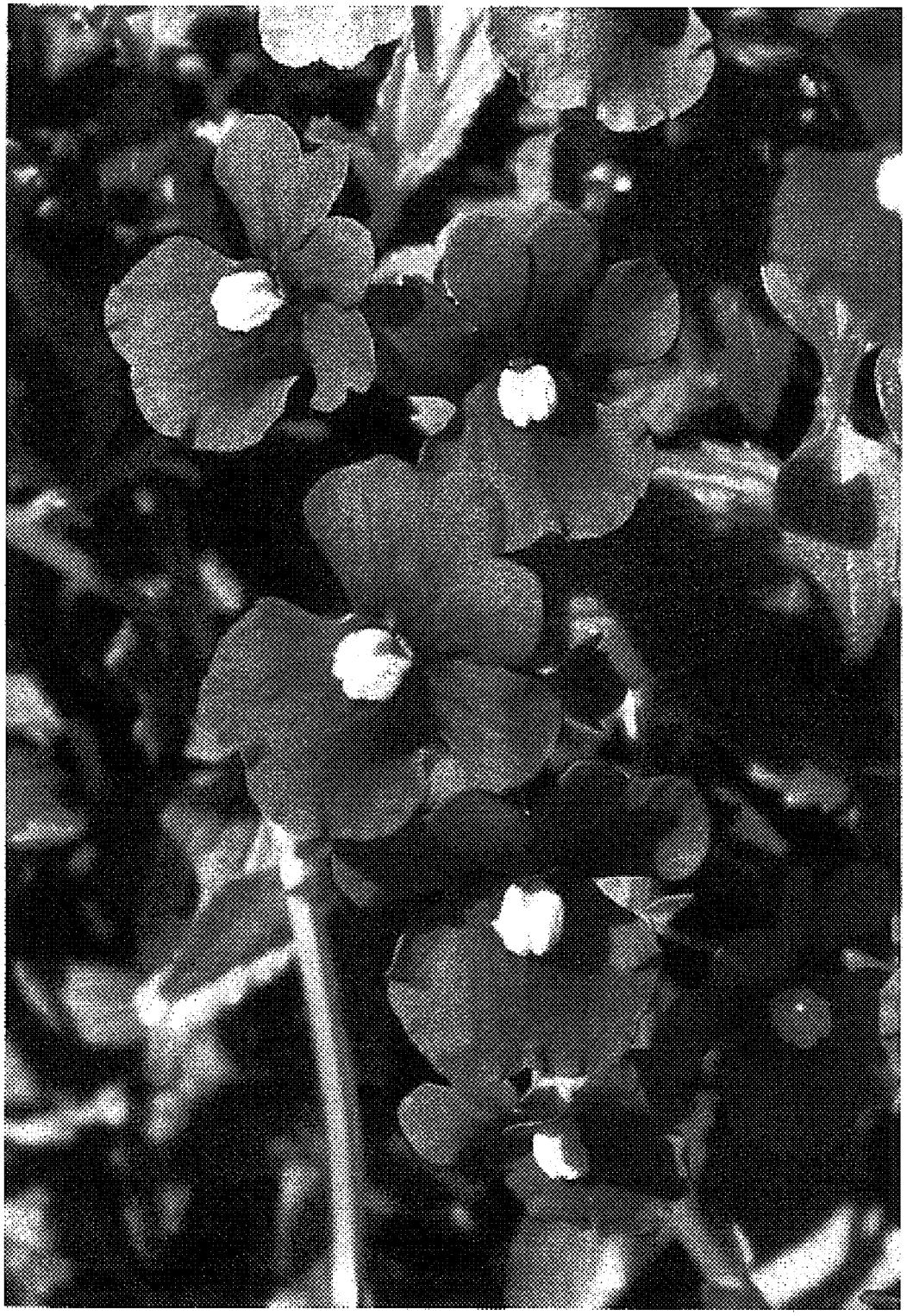
FIG. 2 is a close-up view of the flower. Drawings were made using conventional techniques, and although colors may appear different from actual colors due to light reflectance, they are as accurate as possible by conventional photography.

The following is a detailed description of the new *Nemesia* cultivar named 'FLEURCEL'. Data was collected in Arroyo Grande, Calif. from 4-week-old plants grown indoors in 10 cm. containers. Phenotypic differences may be observed with variations in environmental, climatic, and cultural conditions, without however, any genotypic differences. The color determinations are in accordance with The 2001 Royal Horticultural Society Colour Chart of London, England except where general color terms of ordinary dictionary significance are used. The growing requirements are similar to that of other *Nemesia* plants.

Botanical classification: *Nemesia×hybrida* 'FLEURCEL'.
Family: Scrophulariaceae.
Genus: *Nemesia.*
Species: *×hybrida.*
Denomination: 'FLEURCEL'.
Common name: *Nemesia.*
Plant use: Grown for use as a border plant, hanging basket, or bedding plant.
Parentage: *Nemesia×hybrida* 'FLEURCEL' is a selection arising from the controlled cross-pollination of the following parents:
  *Female parent.*—*Nemesia* Seedling 152.
  *Male parent.*—*Nemesia* Seedling 168.
Asexual plant propagation: Asexual propagation is accomplished using the method of softwood cuttings.
Plant habit: Compact upright habit.
Plant vigor: Vigorous.
Plant dimensions (at maturity): 20 cm. in height and 15 cm in width.
Plant type: Perennial herb.
Soil requirements: 70% medium grade peat, 10% coarse peat, 20% 12 mm. bark with air-filled porosity (AFP) of approximately 17%-19%, and a pH value of approximately 6.0.
Fertilizer requirements: The inventor has found that a combination of fertilizers with the following proportions of Nitrogen, Phosphorus and Potassium produces satisfactory plants with good vigor and flower coloration: (a) N:P:K of 12:14:24 and (b) N:P:K of 14:09:14.
Light requirements: Normal daylight.
Water requirements: Adequate but not excess water.
Time to develop roots on cuttings: Maximum of 14 days.
Required temperature to develop roots: Air temperature of 16° Centigrade and soil temperature of 24° Centigrade.
Crop time: 3 weeks to produce a finished 10 cm. commercial container plant from a rooted cutting.
Seasonal interest: Cerise-red flowers in spring, summer and fall.
Root system: Numerous fine roots.
Plant hardiness: Hardy to minus 6° Centigrade.
Disease and pest susceptibility: 'FLEURCEL' is susceptible to viruses and whitefly.
Special growing requirements: When plugs are transferred to final commercial pots pinch-back to promote fullness.
Stem:
  *Stem shape.*—Quadrangular.
  *Stem dimensions.*—17 cm in length and 3 mm in diameter.
  *Stem surface.*—Glabrous.
  *Stem color.*—144A.
  *Internodes.*—Ranging from 1 cm. to 3 cm.
  *Branching.*—Upright and freely branching.
Foliage:
  *Leaf arrangement.*—Opposite.
  *Leaf shape.*—Ovate.
  *Leaf division.*—Simple.
  *Leaf apex.*—Broadly acute.
  *Leaf base.*—Rounded.
  *Leaf margin.*—Dentate.
  *Leaf surfaces* (*adaxial and abaxial*).—Glabrous.
  *Leaf length.*—Average of 2.50 cm.
  *Leaf width.*—Average of 1.10 cm.
  *Leaf color* (*adaxial surface*).—138A.
  *Leaf color* (*abaxial surface*).—138B.
  *Leaf attachment.*—Combination of petiolate and sessile.
  *Petiole dimensions.*—5 mm long and 3 mm wide.
  *Petiole shape.*—Sulcate.
  *Petiole color.*—138C.
  *Petiole surface.*—Glabrous.
  *Vein pattern.*—Pinnate.
  *Vein color* (*adaxial and abaxial surfaces*).—138C.
Flowers:
  *Type of inflorescence.*—Terminal raceme.
  *Inflorescence dimensions.*—7 cm in length and 3 cm in width.
  *Inflorescence quantity.*—Average of 40 per 10 cm. container.
  *Flowering season.*—Spring, summer and fall.
  *Self-cleaning or persistent.*—Self-cleaning.
  *Pedicel length.*—Average is 1 cm.
  *Pedicel diameter.*—Average is 0.75 mm.
  *Pedicel shape.*—Cylindrical.

*Pedicel surface.*—Stipitate glandular.
*Pedicel color.*—144A.
*Peduncle length.*—Average is 9 cm.
*Peduncle diameter.*—3 mm.
*Peduncle shape.*—Quadrangular.
*Pedundle surface.*—Glabrous.
*Peduncle color.*—144A.
*Bud color.*—*N*79A.
*Bud length.*—Average is 6 mm.
*Bud width.*—Average is 5 mm.
*Bud surface.*—Glabrous.
*Bud apex.*—Obtuse.
*Flower shape.*—Personate.
*Flower depth.*—2.50 cm.
*Flower height.*—1.75 cm.
*Flower width.*—1.50 cm.
*Upper lip dimensions.*—1.60 cm. in width and 1 cm in length.
*Upper lip lobes.*—4 in number.
*Lobe dimensions.*—0.40 cm. in width and 1 cm. in length.
*Lobe shape.*—Elongated rotund.
*Upper lip margin.*—Entire.
*Upper lip apex.*—Obtuse.
*Lower lip dimensions.*—1.25 cm in width and 1 cm in length.
*Lower lip shape.*—Bilabiate.
*Lower lip margin.*—Sinuous.
*Lower lip apex.*—Emarginate.
*Upper and lower lips fused or unfused.*—Basally fused.
*Upper and lower lip surfaces* (*adaxial and abaxial).*—*Glabrous.*
*Upper lip color* (*adaxial surface*).—61A.
*Upper lip color fading to* (*adaxial surface*).—N79B/C.
*Upper lip color* (*abaxial surface*).—79D.
*Lower lip color* (*adaxial surface*).—61A.
*Lower lip color fading to* (*adaxial surface*).—Between N79B and N79C.
*Lower lip color* (*abaxial surface*).—79D.
*Palate color.*—10A.
*Palate dimensions.*—3 mm in height and 3 mm in width.
*Palate surface.*—Glabrous.
*Nectary color.*—3B.
*Nectary surface.*—Lanate.
*Flower spur dimensions.*—0.50 cm in length and 2 mm in diameter.
*Spur color.*—79D.
*Spur surface.*—Glabrous.
*Calyx dimensions.*—7 mm in diameter.
*Calyx shape.*—Stellate.
*Calyx surface.*—Stipitate glandular.
*Sepals.*—Five in number.
*Sepal dimensions.*—3 mm in length and 1.50 mm in width.
*Sepal surface* (*abaxial surface*).—Stipitate glandular.
*Sepal apex.*—Acute.
*Sepal margin.*—Entire.
*Sepal color* (*adaxial and abaxial surfaces*).—144A.
*Sepals fused or unfused.*—Unfused.
*Lastingness of individual flower.*—An individual flower lasts for an average of 5 days.
*Flower fragrance.*—Slightly and pleasantly perfumed.

Reproductive organs:
*Stamens.*—Two in number.
*Stamen color.*—155A.
*Stamen dimensions.*—3 mm in length and less than 1 mm in diameter.
*Anther color.*—161C.
*Anther dimensions.*—Less than 0.50 mm in length and less than 0.50 mm in width.
*Pollen quantity.*—Moderate.
*Pollen color.*—161C.
*Pistil.*—1 in number.
*Pistil color.*—155A.
*Pistil dimensions.*—0.25 mm in length and 0.25 mm in diameter.
*Ovary dimensions.*—0.50 mm in length and 0.50 mm in width.
*Ovary shape.*—Round in shape.
*Ovary position.*—Superior.
*Ovary color.*—145A.

Seed production: No seed has been observed to date.

What is claimed is:

1. A new and distinct cultivar of *Nemesia* plant named 'FLEURCEL' as described and illustrated herein.

* * * * *